(12) United States Patent
Battersby et al.

(10) Patent No.: US 9,719,137 B2
(45) Date of Patent: Aug. 1, 2017

(54) UNIVERSAL TAGS WITH NON-NATURAL NUCLEOBASES

(71) Applicant: Siemens Healthcare Diagnostics Inc., Tarrytown, NY (US)

(72) Inventors: Thomas Battersby, El Cerrito, CA (US); Toumy Guettouche, Miami, FL (US); James Hnatyszyn, Coral Gables, FL (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/196,186

(22) Filed: Jun. 29, 2016

(65) Prior Publication Data

US 2016/0304951 A1    Oct. 20, 2016

Related U.S. Application Data

(62) Division of application No. 14/458,656, filed on Aug. 13, 2014, now Pat. No. 9,404,154, which is a division of application No. 13/318,634, filed as application No. PCT/US2010/035339 on May 19, 2010, now abandoned.

(60) Provisional application No. 61/180,272, filed on May 21, 2009.

(51) Int. Cl.
   *C07H 21/04* (2006.01)
   *C12Q 1/68* (2006.01)
   *C12P 19/34* (2006.01)

(52) U.S. Cl.
   CPC ................... *C12Q 1/6869* (2013.01)

(58) Field of Classification Search
   None
   See application file for complete search history.

(56) References Cited

U.S. PATENT DOCUMENTS

| | | | |
|---|---|---|---|
| 6,225,092 B1 | 5/2001 | Kliger et al. | |
| 8,053,212 B1 | 11/2011 | Benner | |
| 8,614,072 B2 | 12/2013 | Benner et al. | |
| 2003/0148277 A1 | 8/2003 | Chiesa et al. | |
| 2004/0106108 A1* | 6/2004 | Grenier | C12Q 1/6823 435/6.18 |
| 2004/0259118 A1 | 12/2004 | Macevicz et al. | |
| 2006/0172284 A1 | 8/2006 | Zheng et al. | |
| 2006/0172333 A1 | 8/2006 | Chen et al. | |
| 2007/0015200 A1 | 1/2007 | Mayer et al. | |
| 2007/0020667 A1 | 1/2007 | Ruff et al. | |
| 2007/0065860 A1 | 3/2007 | Hildebrand et al. | |
| 2007/0264694 A1 | 11/2007 | Prudent | |
| 2008/0153097 A1 | 6/2008 | Johnson et al. | |
| 2008/0299568 A1 | 12/2008 | Johnson et al. | |

OTHER PUBLICATIONS

Innis et al; DNA sequencing with Thermus aquaticus DNA polymerase and direct sequencing of polymerase chain reaction-amplified DNA Proc Natl Acad Sci 85: 9436-40, (1988).

Johnson, et al., Multiplexed Genetic Analysis Using an Explanded Genetic Alphabet, Clinical Chemistry, 50(11):2019-2027, (2004).

Ugozzoli. Multiplex Assays With Fluorescent Microbead Readout: A Powerful Tool for Mutation Detection, Clinical Chemistry, 50(11): 1963-1965, (2004).

Ahle et al., Sequence Determination of Nucleic Acids Containing 5-Methylisocytosine and Isoguanine: Identification And Insight Into Polymerase Replication of the Non-Natural Nucleobases, Nucleic Acids Research, 33(10):3176-3184, (2005).

Johnson et al., A Third Base Pair for the Polymerase Chain Reaction: Inserting IsoC and IsoG, Nucleic Acids Research, 32(6): 1937-1941, (2004).

International Search Report for WO 2010/135384 dated Nov. 18, 2010.

Sismour et al., "PCR amplification of DNA containing non-standard base pairs by variants of reverse transcriptase from Human Immunodeficiency Virus-1", Nucleic Acid Research, 32(2): 728-735 (2004).

GE Healthcare, DYEnamic ET Terminator Cycle Sequencing Kit, Product Booklet, (2006).

* cited by examiner

*Primary Examiner* — Young J Kim

(57) ABSTRACT

The present invention relates to amplification primers with a universal tag and sequencing primers comprising at least one non-natural nucleobase capable of hybridizing to a complementary non-natural nucleobase. The present invention further relates to amplification methods of nucleic acid amplification and sequencing using an amplification primer with a universal tag and sequencing primers, as well as kits and solid supports comprising such primers and tags.

18 Claims, No Drawings

UNIVERSAL TAGS WITH NON-NATURAL NUCLEOBASES

This application incorporates by reference the sequence listing which is submitted together with this application in computer readable form which has the file name 2009P07981WOUS_ST25.txt and is 4 KB.

This is a divisional application claiming priority from U.S. Ser. No. 14/458,656 filed Aug. 13, 2014 which is a divisional application claiming priority from U.S. Ser. No. 13/318,634 filed Nov. 3, 2011 which is a National Stage of PCT/US2010/035339 filed May 19, 2010, which claims priority from U.S. Ser. No. 61/180,272 filed May 21, 2009, all of which are hereby incorporated by reference herein.

TECHNICAL FIELD OF THE INVENTION

The present invention relates generally to the field of nucleic acids, and more particularly to primer-based amplification and sequence determination of polynucleotides.

BACKGROUND OF THE INVENTION

DNA and RNA constitute the key molecular components of all genetic processes, and have similar structural components. DNA typically exists as a complex of two anti-parallel linear strands or sequences of deoxyribonucleotide structural units, each unit of which consists of a nitrogenous base (adenine (A), thymidine (T), cytosine (C) or guanine (G)), a pentose sugar (a 5-carbon sugar), and a phosphate group. RNA is typically single stranded, and uses uracil (U) in place of thymidine (T). Moreover, the pentose sugar in DNA is 2-deoxyribose, while the pentose sugar in RNA is ribose. The nitrogenous bases of DNA and RNA are of two classes: the larger nine-member double-ring purines, A and G, and smaller six-member single-ring pyrimidines, C, T and U.

The polymerase chain reaction (PCR) presents a very effective method for selectively amplifying specific DNA fragments. In the PCR procedure, oligonucleotides complementary to known segments of the target DNA fragment are added as "primers." The primers serve as starting point for DNA replication enabling PCR amplification. Often, sequencing tags can be included in the primer as a way to identify and or track a gene transcript.

Sequencing of DNA and RNA is an important analytical technique for generating genetic information from biological sources. Sequencing has made possible the determination of DNA and RNA sequences of entire genomes. It is an important diagnostic tool in the clinic, where the rapid detection of a single nucleobase change or a few nucleobase changes can be used to detect, for example, a genetic disease.

SUMMARY OF THE INVENTION

The present invention is generally directed to amplification and sequencing primers having universal tags comprising at least one non-natural nucleobase.

The primers of the invention can be used to amplify polynucleotide templates and incorporate the universal tag in the amplified product. The universal tag can then be used as the template for a universal sequencing primer.

In one particular embodiment of the invention, non-natural isoforms, such as isocytosine (iC) and isoguanine (iG), are added to the 5' tail of sequence-specific amplification primers. Base pairs comprising non-natural isoforms can impart improved stability to duplex nucleic acids and permit the generation of highly specific 5' tails that can be reduced in length (for example, to 10-bases, versus 15-20 bases). A plurality of contiguous non-natural isoforms (such as iC and iG) also prevents DNA polymerase from completing primer extension, thereby preventing sequencing of proprietary 5' tails used in commercial kits by unauthorized parties. Universal sequencing tags can be used to sequence any PCR amplicon. The universal sequence tags incorporating non-natural isoforms are highly specific. Non-natural isoforms can be combined with gene-specific PCR primers containing non-natural nucleobases to facilitate sequencing of genetically diverse targets.

DETAILED DESCRIPTION OF THE INVENTION

Unless defined otherwise, technical and scientific terms used herein have the same meaning as commonly understood by one of ordinary skill in the art to which this invention pertains. Units, prefixes, and symbols may be denoted in their SI accepted form. Unless otherwise indicated, nucleic acid sequences are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic acid sequence discrepancy within the application, the figures control. One skilled in the art will recognize many methods and materials similar or equivalent to those described herein, which could be used in the practice of the present invention. The present invention is in no way limited to the methods and materials described herein, and it is understood that other embodiments of the invention may exist that are not expressly described herein.

Definitions

For purposes of the present invention, the following terms are defined below.

The term "purine-pyrimidine Watson-Crick interaction" as used herein means the interaction of a purine nucleobase and a pyrimidine nucleobase joined through hydrogen bonding in which the N-1 nitrogen atom of the purine is directly opposite the N-3 nitrogen atom of the pyrimidine, the functional group at C-2 (if present) on the purine is directly opposite the functional group at C-2 (if present) on the pyrimidine, and the functional group at C-6 (if present) on the purine is directly opposite the functional group at C-4 (if present) on the pyrimidine. These interactions can exist in both natural and non-natural nucleobases such as purine and pyrimidine analogs in which atoms not directly involved in the base-pairing interaction have been substituted.

The term "nucleobase" as used herein means any nitrogen-containing heterocyclic moiety capable of forming Watson-Crick-type hydrogen bonds and stacking interactions in pairing with a complementary nucleobase or nucleobase analog (i.e., derivatives of nucleobases) when that nucleobase is incorporated into a polymeric structure. "Heterocyclic" refers to a molecule with a ring system in which one or more ring atom is a heteroatom, e.g., nitrogen, oxygen, or sulfur (i.e., not carbon), such as a purine, pyrimidine, or an analog thereof.

A large number of nucleobases, nucleobase analogs and nucleobase derivatives are known. Non-limiting examples of nucleobases include purines and pyrimidines, and modified forms, e.g., 7-deazapurine. Typical nucleobases are the naturally occurring nucleobases adenine, guanine, cytosine, uracil, thymine, and analogs (Seela, U.S. Pat. No. 5,446,139) of the naturally occurring nucleobases, e.g., 7-deazaadenine, 7-deazaguanine, 7-deaza-8-azaguanine, 7-deaza-8-azaadenine, inosine, nebularine, nitropyrrole (Bergstrom, J. Amer. Chem. Soc., 117:1201-1209 [1995]), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990,303), 2-azapurine (Seela, WO 01/16149), 2-thiopyrimidine, 6-thioguanine, 4-thiothymine, 4-thiouracil, O-6-methylguanine, N-6-methyladenine, O-4-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127,121; Gall, WO 01/38584), and ethenoadenine (Fasman (1989) in Practical Handbook of Biochemistry and Molecular Biology, pp. 385-394, CRC Press, Boca Raton, Fla.).

The term "nucleoside" as used herein means a nucleobase linked to a carbohydrate. A nucleobase is coupled to a carbohydrate, for example D-ribose (in RNA) or 2'-deoxy-D-ribose (in DNA), through an N-glycosidic bond between the anomeric carbon of the carbohydrate (1'-carbon atom of the carbohydrate) and the nucleobase. When the nucleobase is purine, e.g., A or G, the ribose sugar is generally attached to the N9-position of the nucleobase. When the nucleobase is pyrimidine, e.g., C, T or U, the sugar is generally attached to the N1-position of the nucleobase. The carbohydrate may be substituted or unsubstituted. Substituted ribose sugars include, but are not limited to, those in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Ribose examples include ribose, 2'-deoxyribose, 2', 3'-dideoxyribose, 2'-haloribose, 2'-fluororibose, 2'-chlororibose, and 2'-alkylribose, e.g., 2'-O-methyl, 4'-alpha-anomeric nucleotides, 1'-alpha-anomeric nucleotides (Asseline et al., Nucl. Acids Res., 19:4067-74 [1991]), 2'-4'- and 3'-4'-linked and other "locked" or "LNA," bicyclic sugar modifications (WO 98/22489; WO 98/39352; WO 99/14226).

Carbohydrates (also called sugars) can include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi et al., Nucl. Acids Res., 21:4159-4165 (1993); Fujimori, J. Amer. Chem. Soc., 112:7435 (1990); Urata, (1993) Nucleic Acids Symposium Ser. No. 29:69-70).

The term "nucleotide" as used herein means a nucleoside in a phosphorylated form—a phosphate ester of a nucleoside, as a monomer unit or within a polynucleotide polymer. "Nucleotide 5'-triphosphate" refers to a nucleotide with a triphosphate ester group at the 5' position, sometimes denoted as "NTP", or "dNTP" and "ddNTP" to particularly point out the structural features of the ribose sugar. The triphosphate ester group may include sulfur substitutions for the various oxygen moieties, e.g., α-thio-nucleotide 5'-triphosphates. Nucleotides can exist in the mono-, di-, or tri-phosphorylated forms. The carbon atoms of the ribose present in nucleotides are designated with a prime character (') to distinguish them from the backbone numbering in the bases. For a review of polynucleotide and nucleic acid chemistry, see Shabarova, Z. and Bogdanov, A. Advanced Organic Chemistry of Nucleic Acids, VCH, New York, 1994. The term "nucleic acid" as used herein means a nucleobase polymer having a backbone of alternating sugar and phosphate units in DNA and RNA. "Nucleic acid" and "polynucleotide" are considered to be equivalent and interchangeable. Nucleic acids are commonly in the form of DNA or RNA.

The term "nucleic acid" includes polynucleotides of genomic DNA or RNA, cDNA, semisynthetic, or synthetic origin. Nucleic acids may also substitute standard nucleotide bases with nucleotide isoform analogs, including, but not limited to iso-C and iso-G bases, which may hybridize more or less permissibly than standard bases, and which will preferentially hybridize with complementary isoform analog bases. Many such isoform bases are described, for example, by Benner et al., (1987) Cold Spring Harb. Symp. Quant. Biol. 52, 53-63. In representations of degenerate primers or mixture of different strands having mutations in one or several positions, the symbol R refers to either G or A, the symbol Y refers to either T/U or C, the symbol M refers to either A or C, the symbol K refers to either G or T/U, the symbol S refers to G or C, the symbol W refers to either A or T/U, the symbol B refers to "not A," the symbol D refers to "not C," the symbol H refers to "not G," the symbol V refers to "not T/U" and the symbol N refers to any nucleotide.

"Polynucleotide" and "oligonucleotides" are used interchangeably and mean single-stranded and double-stranded polymers of nucleotide monomers, including 2'-deoxyribonucleotides (DNA) and ribonucleotides (RNA) linked by internucleotide phosphodiester bond linkages, (e.g., 3'-5', and 2'-5'), inverted internucleotide phosphodiester bond linkages (e.g., 3'-3' and 5'-5'), branched structures, or internucleotide analogs. A "polynucleotide sequence" refers to the sequence of nucleotide monomers along the polymer. "Polynucleotides" are not limited to any particular length of nucleotide sequence, as the term "polynucleotides" encompasses polymeric forms of nucleotides of any length. Polynucleotides that range in size from about 5 to about 40 monomeric units are typically referred to in the art as oligonucleotides. Polynucleotides that are several thousands or more monomeric nucleotide units in length are typically referred to as nucleic acids. Polynucleotides can be linear, branched linear, or circular molecules. Polynucleotides also have associated counter ions, such as H$^+$, NH$_4^+$, trialkylammonium, Mg$^{2+}$, Na$^+$ and the like.

Polynucleotides that are formed by 3'-5' phosphodiester linkages are said to have 5'-ends and 3'-ends because the mononucleotides that are reacted to make the polynucleotide are joined in such a manner that the 5' phosphate of one mononucleotide pentose ring is attached to the 3' oxygen (i.e., hydroxyl) of its neighbor in one direction via the phosphodiester linkage. Thus, the 5'-end of a polynucleotide molecule has a free phosphate group or a hydroxyl at the 5' position of the pentose ring of the nucleotide, while the 3' end of the polynucleotide molecule has a free phosphate or hydroxyl group at the 3' position of the pentose ring. Within a polynucleotide molecule, a position or sequence that is oriented 5' relative to another position or sequence is said to be located "upstream," while a position that is 3' to another position is said to be "downstream." This terminology reflects the fact that polymerases proceed and extend a polynucleotide chain in a 5' to 3' fashion along the template strand.

A polynucleotide may be composed entirely of deoxyribonucleotides, entirely of ribonucleotides, or chimeric mixtures thereof. Polynucleotides may be composed of internucleotide nucleobase and sugar analogs. Unless denoted otherwise, whenever a polynucleotide sequence is represented, it will be understood that the nucleotides are in 5' to 3' orientation from left to right.

The term "heteropolynucleotide" means a polynucleotide comprising more than one nucleobase type.

The term "duplex" means a bimolecular nucleic acid complex, usually formed through association of a series of interacting nucleobase dyads, one from each molecule of the complex. A single nucleic acid molecule may also have regions of duplex association by folding back onto itself and intramolecularly hybridizing to a complementary sequence.

The term "complementary" means that two nucleobases are capable of associating in a Watson-Crick interaction of potential hydrogen bonding functionality without repulsive interaction(s). "Complementary" also means that a nucleobase of a polynucleotide is capable of hybridizing to a corresponding nucleobase in a different polynucleotide. As used herein, the term "complementary" is not limited to canonical Watson-Crick base pairs with A/T, G/C and U/A. Thus, nucleobase pairs may be considered to be "complementary" if one or both of the nucleobases is a nucleobase other than A, G, C, or T. The term "complementary" also refers to antiparallel strands of polynucleotides (as opposed to a single nucleobase pair) that are capable of hybridizing. Thus, complementary strands have a sufficient number of complementary nucleobases to enable hybridization of the two strands. It should be understood that complementary strands of polynucleotides can include some corresponding base pairs that are non-complementary. Accordingly, it should also be understood that corresponding nucleobase pairs need not be complementary. The term "complementary" as used in reference to two nucleotide sequences or two nucleobases, implies that the nucleotide sequences or nucleobases are "corresponding."

The terms "capable of hybridizing" mean that at least two nucleobases can form a dyad or that a polynucleotide has a sufficient number of nucleobases complementary to another polynucleotide that they can anneal and form a duplex.

The term "target-specific nucleotide sequence" means a nucleic acid sequence that is the native sequence of interest. It may be a gene, a regulatory sequence, genomic DNA, mRNA, or others or a portion of any of the foregoing. It may be any length, with the understanding that longer sequences are more specific.

The term "comprising" means the listed elements, plus any additional unspecified elements.

The term "consisting essentially of" means the listed elements, plus any additional unspecified elements that do not function as a nucleobase dyad. Thus, with respect to claims reciting polynucleotide duplexes "consisting essentially of" a plurality of complementary purine-purine nucleobase dyads, the term "consisting essentially of" is used to characterize only the nucleobase dyads, and thus the claim is open to the inclusion of other elements that are not nucleobase dyads, such as pentose sugar backbones, phosphate groups, detectable labels, and cross-linking agents, etc.

The term "corresponding" when used to refer to two nucleotide sequences or two nucleobases within a sequence means having the same or nearly the same relationship with respect to position and complementarity, or having the same or nearly the same relationship with respect to structure, function, or genetic coding (for example, as between a gene and the "corresponding" protein encoded by the gene). For example, a nucleotide sequence "corresponds" to a region of a polynucleotide template if the two sequences are complementary or have portions that are complementary. Similarly, a nucleobase of an oligomer "corresponds" to a nucleobase of a polynucleotide template when the two nucleobases occupy positions such that when the oligomer and the polynucleotide hybridize the two nucleobases pair opposite each other. The term "corresponding" is generally used herein in reference to the positional relationship between two polynucleotide sequences or two nucleobases. The term "corresponding" does not imply complementarity; thus, corresponding nucleobases may be complementary, or may be non-complementary.

The term "dyad" means two nucleobases or analogs paired within a duplex, one from each opposing strand of the duplex.

The term "backbone" means a repeating linear polymer to which nucleobases or analogs are attached. In DNA the backbone is formed by alternating 2'-deoxy-D-ribose and phosphate units. In RNA the backbone is formed by alternating D-ribose and phosphate units.

The phrase "hydrogen bonding pattern" means the hydrogen bonding pattern of acceptor (A) and donor (D) groups of a pyrimidine or pyrimidine analog (py) and a purine or purine analog (pu) molecule, designated using the nomenclature of Benner (Lutz, et al. Differential discrimination of DNA polymerases for variants of the non-standard nucleobase pair between xanthosine and 2,4-diaminopyrimidine, two components of an expanded genetic alphabet, Nucleic Acids Res. 24:1308-1313 (1996)). The term "pu" as used herein denotes a carbon/nitrogen heterocycle isosteric to the ring system of purines (i.e., adenine and guanine) with a nitrogen atom at position 1. Functionality capable of acting as hydrogen bond donors or acceptors in Watson-Crick interaction may be present at the carbon atoms of positions 2 and 6. The nature of this functionality, if present, is indicated by a series of three symbols representing positions moving around the pu ring from position 6 to position 1 to position 2 ("D"=H bond donor, "A"=H bond acceptor, "_"=no functionality). Similarly, the term "py" as used herein denotes a carbon/nitrogen heterocycle isosteric to the ring system of pyrimidines (i.e., thymine/uracil and cytosine) with a nitrogen atom at position 3. Functionality capable of acting as hydrogen bond donors or acceptors in Watson-Crick interaction may be present at the carbon atoms of positions 2 and 4. The nature of this functionality, if present, is indicated by a series of three symbols representing positions moving around the py ring from position 4 to position 3 to position 2 ("D"=H bond donor, "A"=H bond acceptor, "_"=no functionality).

The hydrogen bonding patterns of the natural purines are denoted as puDA (adenine) and puADD (guanine). Similarly, the hydrogen bonding patterns of the natural pyrimidines are pyDAA (cytosine) and pyADA (thymine/uracil). Thus, the notation representing cytosine-guanine bonding pattern is pyDAA-puADD, and the thymine/uracil-adenine bonding pattern is pyADA-puDA.

The term "ribose" as used herein means a pentose sugar of the general formula $C_5H_{10}O_5$ occurring as a component of riboflavin, nucleotides, and nucleic acids.

The term "deoxyribose" as used herein means any of certain pentose carbohydrates derived from ribose by the replacement of a hydroxyl group with a hydrogen atom of the general formula $C_5H_{10}O_4$.

The term "non-natural nucleobase" means a nucleobase other than G, C, T/U or A. In some embodiments, the non-natural nucleobases for Watson-Crick complementary nucleobase pair analogs having hydrogen bonding interactions that can be discriminated from natural nucleobase pairs. It should be understood that non-natural nucleobases can complement one another without engaging in Watson-Crick complementarity.

The term "phosphate" as used herein means a salt or ester of phosphoric acid.

The abbreviation "Tm" as used herein means the "melting temperature." The melting temperature is the temperature at which half of a population of double-stranded polynucleotide molecules or nucleobase oligomers, in homoduplexes or heteroduplexes, become dissociated into single strands. The Tm of a double-stranded nucleobase oligomeric molecule is influenced by the types of bases, the base sequence, structure of the oligomeric linkages, and the presence of non-natural features in the sequence, which would included, for example, artificial linkages. Methods for calculating or experimentally determining Tm are known in the art. See, for example, Breslauer et al. Proc. Natl. Acad. Sci. USA 83: 3746-3750 (1986); Baldino et al. Methods in Enzymol. 168: 761-777 (1989); and Breslauer Methods in Enzymol. 259: 221-242 (1995).

The term "antiparallel" is used to refer to interaction in which an oligonucleotide strand oriented in the 5'-3' direction is hybridized to a complementary strand oriented in the 3'-5' direction.

The term "stable" as used in reference to a heteropolynucleotide duplex, means that the duplex remains hybridized essentially exclusively in the form of a duplex under typical salt and temperature conditions used in nucleic acid diagnostic applications.

The term "universal tag" as used herein means an oligonucleotide sequence having at least one (i.e. one or more) non-natural nucleobase. The universal tag can be replicated during amplification prior to a subsequent sequencing reaction. A portion of the universal tag may also be replicated during sequencing until the replication reaches a first non-natural nucleobase in the tag. A universal tag can refer to both the sequence and its complement created during amplification. Universal tags can be used to simplify sequencing or act as a marker for sequence identification or purification. Universal tags can be used to identify amplicons. Universal tags can also be used to purify and/or isolate amplicons with the universal tag. For example, a complementary oligonucleotide to the universal tag may be immobilized on a surface for hybridization to the tag, thereby separating the amplicon from a mixture of oligonucleotide sequences. A universal tag should not be complementary to any sequence of a polynucleotide template or any other template present in a sample. The universal tag is non-target specific in relation to the target template.

The practice of the present invention will employ, unless otherwise indicated, conventional techniques of molecular biology, microbiology, recombinant DNA techniques, and oligonucleotide synthesis which are within the skill of the artisan. Such techniques are explained fully in the literature. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See, e.g., Sambrook et al. Molecular Cloning: A Laboratory Manual (2d ed., Cold Spring Harbor Laboratory Press, Cold Spring Harbor, N.Y. (1989)); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.), the contents of all of which are incorporated herein by reference.

Universal Tags Incorporating Non-Natural Nucleobases

As is known in the art, DNA (e.g., a DNA template) is amplified by the polymerase chain reaction process, using two oligonucleotide extension primers—one that is complementary to a first locus on one strand of the DNA, and a second that is complementary to a different or second locus on the other strand of the DNA. The region between the two loci is the region of the original DNA template that is amplified. The amplified product includes a DNA sequence between and including the two primers that hybridize to the original template (i.e. amplicons). Primers may also include tags, which can be incorporated into the amplified product.

The oligonucleotide amplification primers of the present invention include improved universal tags that comprise non-natural nucleobases. In some embodiments, the primers include (i) a target-specific nucleotide sequence and (ii) a 5' non-target-specific universal tag comprising one or more non-natural nucleobases. Amplification of a template polynucleotide results in amplification products that incorporate the universal tag having the non-natural nucleobases. The non-natural nucleobases are capable of complementary binding to a complementary second non-natural nucleobase.

For example, in the first cycle of amplification, the double-stranded DNA is separated to provide two DNA templates (the sense strand and the complementary antisense strand). The target-specific sequence of one amplification primer initially binds to its complementary first locus on one of these strands, while the target-specific sequence of the other amplification primer binds to its complementary second locus on the other strand. The 5' non-target-specific universal tag regions of the primers do not participate in hybridization to the DNA template, since the tags, by definition, are "non-target specific" (i.e., they are not complementary) and cannot therefore hybridize to any region of the template. Primer extension of both amplification primers is initiated (using a DNA polymerase and appropriate ddNTP nucleotide building blocks) to add additional nucleotides to the primer downstream of the target-specific sequence, thereby producing newly synthesized second strands that are complementary to the target DNA and which also include the 5' non-target-specific universal tag.

In the second cycle of amplification, this second strand then becomes a template for the other amplification primer which hybridizes to the other locus downstream of the universal tag on the newly synthesized DNA strand. Primer extension of both amplification primers is again initiated. Because the 5' non-target-specific universal tag is now part of the DNA template (derived from the newly synthesized DNA strand from the first cycle), primer extension of the target-specific nucleotide sequence (using a primer specific for the other DNA locus and also having a 5' non-targetspecific universal sequencing tag) adds nucleotides corresponding to the target DNA region, as well as a 5' non-target-specific universal tag. The newly synthesized DNA sequence from this second cycle now includes the sequence between and including the two primers in the original template, including the universal tag sequence at each end of the newly synthesized DNA sequence, corresponding to the universal tag sequences of each of the two primers. In subsequent amplification cycles, the DNA templates will include the sequence between and including the two primers in the original template and the universal tag sequences at each end, providing complementary sequence to which the 5' non-target-specific universal tags of the primers can hybridize.

Methods for using universal tags and applications are disclosed, for example, in U.S. Patent Publication 2003/02919751 A1, Nov. 27, 2003.

A 5' non-target-specific sequencing tag comprises one or more non-natural nucleobases capable of complementary binding to a complementary second non-natural nucleobase. Incorporation of non-natural nucleobases in the 5' non-target-specific universal tag has numerous advantages. One advantage is that certain non-natural nucleobase pairs hybridize with higher affinity than natural nucleobase pairs. The higher affinity of non-natural nucleobase pairs (compared to natural nucleobase pairs GC and AT) increases the melting temperature of duplexes that include the non-natural nucleobase pairs. Certain non-natural nucleobase pairs, such as iC-iG pairs, for example, have greater thermodynamic duplex stability than natural nucleobase pairs G-C or A-T. Since the stringency of binding is controlled by temperature, the temperature can be adjusted so that the specificity of the primer including non-natural bases will be higher than a primer without non-natural bases, thereby allowing discrimination of duplexes having the non-natural nucleobases from duplexes having only natural nucleobases. In addition, at a given temperature, a shorter primer length may be used when non-natural nucleobase pairs (such as iC-iG) are incorporated than when they are not. Another advantage of using universal sequencing tags arises from obviating the need to perform any screening of sequencing reaction conditions.

Another advantage of incorporating a plurality of non-natural isoforms into the universal tag is that it prevents DNA polymerase from completing primer extension, which property can be used, for example, to prevent unauthorized parties from sequencing proprietary 5' tails used in commercial kits. Thus, in some embodiments, a universal tag may include a plurality of contiguous non-natural nucleobase isoforms. The plurality of contiguous non-natural nucleobase isoforms are incorporated at or near the junction of (i.e., between) the (i) a target-specific nucleotide sequence and (ii) a 5' non-target-specific universal sequencing tag. Extension of the target-specific primer from the 3' to the 5' direction (new ddNTP, dNTP, and NTP nucleotides are added to the primer in the 5' to 3' direction of the primer but in the 3' to the 5' direction of the template) terminates when the polymerase enzyme reaches the block of contiguous non-natural nucleobases following the target-specific nucleotide sequence, preventing the polymerase sequencing enzyme from entering a region of the universal tag downstream of the non-natural nucleobases and preventing the user from obtaining the nucleotide sequence of the universal tag. This approach enables manufacturers of kits to protect the identity of proprietary universal tag sequences, and prevent users from using the universal tag sequence without a manufacturer's permission.

In some embodiments, amplification is followed by sequencing. The oligonucleotide amplification primers used in these processes include a universal sequencing tag, which incorporates the universal sequencing tag into the amplification products. The amplified products derived from primers with the universal sequencing tag include the DNA sequence between and including the two primers that hybridize to the original template, as well as the universal tags at the end of each amplification product. Thus, the primers include (i) a target-specific nucleotide sequence and (ii) a 5' non-target-specific universal sequencing tag comprising one or more non-natural nucleobases. The non-natural nucleobases are capable of complementary binding to a complementary second non-natural nucleobase. The universal sequencing tag can then be used to identify and/or isolate the amplification products, or to sequence the amplification products using sequencing primers that are complementary to the sequencing tags and include non-natural nucleobases that are complementary to the non-natural nucleobases of the universal tags incorporated into the amplification products. Sequencing can be performed via monodirectional or bidirectional sequencing. Bidirectional sequencing involves simultaneous sequencing on each of the component strands of a duplex. Thus, from the perspective of a given strand, information is obtained for the 5' to 3' direction and for the 3' to 5' direction of the duplex.

In accordance with the present invention, primers with a 3' target-specific nucleotide sequence and a 5' non-target-specific universal tag comprising one or more non-natural nucleobase(s) capable of hybridizing to a complementary non-natural nucleobase are described. In one embodiment, the non-natural nucleobases include nucleobases that can associate through Watson-Crick pairing of purine-pyrimidine nucleic acid duplexes. In another embodiment, the non-natural nucleobases include nucleobases that can associate through non-Watson-Crick pairing such as those described in Leconte, A. M., et al., "Discovery, characterization, and optimization of an unnatural base pair for expansion of the genetic alphabet." J. Am. Chem. Soc. 130(7):2336-43; and Hirao, K., et al., Nat. Methods 2006, 3, 729-735. These non-natural nucleobases form a base pair that is replicatable, that is they are a matched pair to the polymerase in use. Non-Waston-Crick pairing non-natural nucleobases have good affinity in a duplex structure and are replicatable by a polymerase.

The purine-pyrimidine nucleic acid duplexes can include a N3-H tautomer of isoguanine.

In one aspect, a universal tag comprises at least one (i.e. one or more) non-natural nucleobase capable of forming purine-pyrimidine nucleobase dyads. The nucleic acids may further comprise a carbohydrate backbone of ribose or deoxyribose, and phosphate.

In another aspect, a universal tag is disclosed consisting essentially of a plurality of non-natural nucleobases capable of forming complementary purine-pyrimidine nucleobase dyads. The nucleic acids may further comprise a carbohydrate backbone of ribose or deoxyribose, and phosphate. Suitable carbohydrate backbones include, for example, D-ribose and 2'-deoxy-D-ribose.

The universal tag can form one or more nucleobase dyads with other nucleobases through purine-pyrimidine pairing through complementary Watson-Crick interactions. In some embodiments, the universal tag can form complementary purine-pyrimidine nucleobase dyads that are contiguous. In some embodiments, the universal tag can form complementary purine-pyrimidine nucleobase dyads that are not contiguous.

The universal tag can include a nucleobase adopting a tautomer that is a minor species of the nucleobase present in aqueous solution (i.e., an unhybridized nucleobase) in the absence a Watson-Crick interaction.

In some embodiments, one or more of the non-natural nucleobases are selected from the group of purine and pyrimidine analogs capable of Watson-Crick pairing through formation of 2 or 3 hydrogen bonds. For example, non-natural nucleobases may form nucleic acid duplexes with one or more purine-pyrimidine nucleobase dyads may have the following hydrogen bond donor and acceptor pairings:

| | | |
|---|---|---|
| puADD-pyDAA | puAD_-pyDAA | puAD_-pyDA_ |
| | puADD-py_AA | pu_DD-py_AA |
| puDAD-pyADA | puDA_-pyADA | puDA_-pyAD_ |
| | pu_AD-pyADA | pu_AD-py_DA |
| puDDA-pyAAD | pu_DA-pyAAD | pu_DA-py_AD |
| | puDDA-pyAA_ | puDD_-pyAA_ |
| puDAA-pyADD | pu_AA-pyADD | pu_AA-py_DD |
| | puDAA-pyAD_ | puDA_-pyAD_ |
| puADA-pyDAD | puADA-py_AD | pu_DA-py_AD |
| | puADA-pyDA_ | puAD_-pyDA_ |
| puAAD-pyDDA | puAA_-pyDDA | puAA_-pyDD_ |
| | puAAD-py_DA | pu_AD-py_DA |

The universal tag can form a nucleic acid duplex can comprising nucleobase dyads having the above hydrogen bond donor and acceptor pairings with one or both of the nucleobases of the dyad adopting a tautomer that is a minor species present in aqueous solution in the absence a Watson-Crick interaction.

In some embodiments, the universal tags incorporating one or more non-natural nucleic acids can comprise a plurality of contiguous purine-pyrimidine dyads with non-natural nucleobases. In one embodiment, the universal tags incorporating one or more non-natural nucleic acids comprise at least 3 contiguous purine-pyrimidine nucleobase dyads with non-natural nucleobases. In another embodiment, the universal tags incorporating one or more non-natural nucleic acids comprise at least 4 contiguous purine-pyrimidine nucleobase dyads with non-natural nucleobases. In still another embodiment, the universal tags incorporating one or more non-natural nucleic acids comprise at least 5 contiguous purine-pyrimidine nucleobase dyads with non-natural nucleobases.

In some embodiments, the universal tags incorporating a plurality of non-natural nucleic acids can comprise at least one non-natural purine capable of forming a dyad with another purine nucleobase and a plurality of non-natural purine nucleobases capable of forming purine-pyrimidine nucleobase dyads. In another embodiment, the universal tags incorporating a plurality of non-natural nucleic acids can comprise a plurality of not natural purine nucleobases capable of forming purine-purine nucleobase dyads and a plurality of non-natural purine nucleobases capable of forming purine-pyrimidine nucleobase dyads.

In some embodiments, one or more of the non-natural nucleobases are independently selected from the group consisting of isocytosine, isoguanine and 5-methylisocytosine. In one embodiment, as least one non-natural nucleobase is isocytosine. In one embodiment, as least one non-natural nucleobase is isoguanine. In one embodiment, as least one non-natural nucleobase is 5-methylisocytosine.

In some embodiments, one or more of the non-natural nucleobases are contiguous to the target-specific nucleotide sequence.

In some embodiments, one or more of the non-natural nucleobases are positioned 3' of a least a portion of a target-specific nucleotide sequence.

In some embodiments, the non-natural nucleobases are selected from the group consisting of Watson-Crick complementary nucleobase analogs having hydrogen bonding interactions that can be discriminated from natural nucleobase pairs.

Amplified Polynucleotide Templates

In another aspect, an amplified polynucleotide template comprises (a) a 3' target-specific nucleotide sequence and (b) a 5' universal tag comprising at least one (i.e one or more) non-natural nucleobase, each non-natural nucleobases of which is complementary to a non-natural nucleobase of a complementary polynucleotide. In some embodiments, the 5' universal tag comprises a plurality of non-natural nucleobases, each non-natural nucleobases of which is complementary to a non-natural nucleobase of a complementary polynucleotide. In some embodiments, the polynucleotide template is a sequencing template with a 5' universal sequencing tag.

Nucleic Acid Duplex

In another aspect, a nucleic acid duplex comprises an oligonucleotide primer comprising (a) a 3' target-specific nucleotide sequence and (b) a 5' non-target-specfic universal tag comprising at least one (i.e. one or more) non-natural nucleobase capable of complementary binding to a corresponding second non-natural nucleobase wherein the oligonucleotide is hybridized to a polynucleotide target.

In one embodiment, a nucleic acid duplex comprises (a) a universal tag further comprising (i) a target-specific nucleotide sequence and (ii) a 5' universal tag comprising a non-natural nucleobase complementary to a corresponding non-natural nucleobase hybridized to (b) an amplified polynucleotide template comprising (i) a target polynucleotide and (ii) a 5' universal tag comprising at least one (i.e. one or more) non-natural nucleobase. In some embodiments, the polynucleotide template is a sequencing template with a 5' universal sequencing tag.

Amplification

In another aspect, a method of amplifying a polynucleotide molecule includes providing a polynucleotide molecule, contacting the polynucleotide molecule with an oligonucleotide primer, wherein the oligonucleotide primer comprises a 3' nucleotide sequence complementary to the polynucleotide molecule and a 5' non-target-specific universal tag comprising at least one non-natural nucleobase capable of hybridizing to a complementary non-natural nucleobase. Amplicons prepared in this manner will have the universal tag. In some embodiments, the universal tag will be a universal sequencing tag so that the amplicons derived therefrom can be sequenced with universal sequencing tag.

Hybridization

In another aspect, a polynucleotide molecule with a universal tag can be hybridized to a complementary polynucleotide molecule. The first polynucleotide molecule possesses a first universal tag. The first polynucleotide molecule hybridizes to a second polynucleotide molecule by contacting a second polynucleotide molecule that is complementary to the first polynucleotide molecule, and the second polynucleotide molecule has a second universal tag complementary to the first universal tag present in the first polynucleotide molecule.

In one embodiment, the first polynucleotide molecule comprises a region consisting of a plurality of non-natural purine and non-natural pyrimidine nucleotides coupled to a backbone consisting of ribose or deoxyribose, and phosphate. The first polynucleotide molecule after contacting the second polynucleotide molecule hybridizes to the second polynucleotide molecule comprising a plurality of complementary non-natural pyrimidine and non-natural purine nucleotides coupled to a backbone consisting of ribose or deoxyribose, and phosphate, wherein the nucleotides of the first polynucleotide molecule are complementary to the nucleotides of the second polynucleotide molecule, thereby forming a stable anti-parallel nucleic acid duplex.

In one embodiment the first polynucleotide molecule comprises a region consisting of a plurality of non-natural purine nucleotides coupled to a backbone consisting of ribose or deoxyribose, and phosphate. The first polynucleotide molecule after contacting the second polynucleotide molecule hybridizes to the second polynucleotide molecule comprising a plurality of pyrimidine nucleotides coupled to a backbone consisting of ribose or deoxyribose, and phosphate, wherein the purine nucleotides of the first polynucleotide molecule are complementary to the plurality of non-natural pyrimidine nucleotides of the second polynucleotide molecule, thereby forming a stable anti-parallel nucleic acid duplex.

In another embodiment the first polynucleotide molecule comprises a region consisting of a plurality of non-natural pyrimidine nucleotides coupled to a backbone consisting of ribose or deoxyribose, and phosphate. The first polynucleotide molecule after contacting the second polynucleotide molecule hybridizes to the second polynucleotide molecule comprising a plurality of purine nucleotides coupled to a backbone consisting of ribose or deoxyribose, and phosphate, wherein the pyrimidine nucleotides of the first polynucleotide molecule are complementary to the plurality of non-natural purine nucleotides of the second polynucleotide molecule, thereby forming a stable anti-parallel nucleic acid duplex.

In some embodiments, a method of hybridizing two nucleic acid molecules includes providing a first polynucleotide molecule comprising a first universal tag having one or more regions consisting of a plurality of purine nucleotides coupled to a backbone of ribose or deoxyribose, and phosphate, and hybridizing a second polynucleotide molecule comprising a second universal tag having one or more regions consisting of a plurality of pyrimidine nucleotides coupled to a backbone consisting of ribose or deoxyribose, and phosphate, wherein the one or more regions of a plurality of purine nucleotides of the first universal tag complement the pyrimidine nucleotides of the second universal tag, thereby forming a stable anti-parallel nucleic acid duplex having a plurality of purine-pyrimidine dyads. In some embodiments, the plurality of non-natural purine nucleotides comprising at least one non-natural nucleobase contains a plurality of non-natural nucleobases. In some embodiments, the non-natural nucleobases are contiguous. In some embodiments, the non-natural nucleobases are not contiguous.

In some embodiments, a method of hybridizing two nucleic acid molecules includes providing a first polynucleotide molecule comprising a first universal tag having one or more regions consisting of a plurality of purine and pyrimidine nucleotides coupled to a backbone of ribose or deoxyribose, and phosphate, and hybridizing a second polynucleotide molecule comprising a second universal tag having one or more regions consisting of a plurality of pyrimidine and purine nucleotides coupled to a backbone consisting of ribose or deoxyribose, and phosphate, wherein the one or more regions of a plurality of purine and pyrimidine nucleotides of the first universal tag complement the pyrimidine and purine nucleotides of the second universal tag, thereby forming a stable anti-parallel nucleic acid duplex having a plurality of purine-pyrimidine dyads. In some embodiments, the plurality of purine and pyrimidine nucleotides comprising at least one non-natural nucleobase contains a plurality of non-natural nucleobases. In some embodiments, the non-natural nucleobases are contiguous. In some embodiments, the non-natural nucleobases are not contiguous.

Labeling of Oligonucleotides

Universal tags with a target-specific nucleotide sequence and a 5' universal tag comprising at least one non-natural nucleobase complementary to a corresponding non-natural nucleobase can also be labeled with a suitable label/reporter moiety. For example, the universal tags may be labeled with a label or with multiple labels selected from the group of labels consisting of dyes, fluorescent labels, luminescent labels, radioactive labels, antigens, haptens, enzymes, enzyme substrates, protecting groups, and chemically reactive groups. Other labels may also be used, in addition to, or in conjunction with, these labels.

As used herein, the term "label" in reference to universal tags refers to any moiety that can be attached to the tag and: (i) provides a detectable signal, where the signal can be in the visible wavelength spectrum or any other wavelength or particle type, e.g., a radioisotope decay particle; (ii) interacts with a second label to modify the detectable signal provided by the second label, i.e., energy transfer label pairs, e.g., FRET pairs; (iii) stabilizes hybridization, i.e., duplex formation; (iv) confers a capture function, e.g., hydrophobic affinity, antibody/antigen, ionic complexation, or (v) changes a physical property, such as electrophoretic mobility, hydrophobicity, hydrophilicity, solubility, or chromatographic behavior. Labeling can be accomplished using any one of a large number of known techniques employing known labels, linkages, linking groups, reagents, reaction conditions, and analysis and purification methods. Labels include light-emitting or light-absorbing compounds which generate or quench a detectable fluorescent, chemiluminescent, or bioluminescent signal (Kricka, L. in Nonisotopic DNA Probe Techniques (1992), Academic Press, San Diego, pp. 3-28). As used herein, the terms "label" and "reporter" may in some cases be used interchangeably.

It is contemplated that the universal tags can be labeled with any labeling moiety or technique currently known in the art for labeling nucleic acids, modified nucleic acids or nucleic acid analogs. It is not intended that the invention be limited in any way to any particular labeling method. Techniques for labeling of nucleic acids, modified nucleic acids and nucleic acid analogs are widely known in the art, and thorough discussion and detailed protocols for labeling are available from many sources. For example, see, "Non-Radioactive Labeling, A Practical Introduction," Garman, Academic Press, San Diego, Calif. (1997).

Non-limiting examples of reporter/label moieties suitable for the direct labeling of oligonucleotides include, but are not limited to, a quantum dot, a dextran conjugate, a branched nucleic acid detection system, a chromophore, a fluorophore, a quencher, a spin label, a radioisotope, an enzyme, a hapten, an acridinium ester and a chemiluminescent compound. Quenching moieties are also considered labels. Other suitable labeling reagents and preferred methods of label attachment would be recognized by those of ordinary skill in the art. Any examples cited herein are intended to be merely illustrative and are non-limiting A label or reporter moiety can be linked to any position within a nucleobase oligomers within the universal tag. A label can reside at a terminus of the universal tag or at a position internal to the universal tags (e.g., within or attached to the nucleobases). The nucleobase can be labeled either following synthesis of the complete universal tag or incorporated during amplification of a target nucleotide sequence.

Non-limiting examples of fluorescent reporter dyes useful for labeling biomolecules (fluorophores) include, but are not limited to, 5(6)-carboxyfluorescein (Flu), 2',4',1,4,-tetra-chlorofluorescein; and 2',4',5',7',1,4-hexachlorofluoresc-ein, other fluorescein dyes (see, e.g., U.S. Pat. Nos. 5,188,934; 6,008,379; 6,020,481, incorporated herein by reference), 6-((7-amino-4-methylcoumarin-3-acetyl)amino)hexanoic acid (Cou), 5(and 6)-carboxy-X-rhodamine (Rox), other rhodamine dyes (see, e.g., U.S. Pat. Nos. 5,366,860; 5,847, 162; 5,936,087; 6,051,719; 6,191,278; 6,248,884, incorporated herein by reference), benzophenoxazines (see, e.g., U.S. Pat. No. 6,140,500, incorporated herein by reference) Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.), other cyanine dyes (Kubista, WO 97/45539), 6-carboxy-4',5'-dichloro-2',7'-dimethoxyfluorescein (JOE), 5(6)-carboxy-tetramethyl rhodamine (Tamara), Dye 1 Dye2 or the Alexa dye series (Molecular Probes, Eugene, Oreg.).

Non-limiting examples of enzymes that can be used as labels include, but are not limited to, alkaline phosphatase (AP), horseradish peroxidase (HRP), soy bean peroxidase (SBP), ribonuclease and protease.

Another class of labels includes hybridization-stabilizing moieties which serve to enhance, stabilize, or influence hybridization of duplexes and cross-linking functional groups (Blackburn and Gait, Eds., "DNA and RNA Structure" in Nucleic Acids in Chemistry and Biology, 2nd Edition, (1996) Oxford University Press, pp. 15-81). Yet another class of labels affects the separation or immobilization of a molecule by specific or non-specific capture, for example biotin, digoxigenin, and other haptens (Andrus, "Chemical methods for 5' non-isotopic labeling of PCR probes and primers" (1995) in PCR 2: A Practical Approach, Oxford University Press, Oxford, pp. 39-54). Suitable haptens include fluorescein, biotin, 2,4-dinitrophenyl, digoxigenin, lipopolysaccharide; apotransferrin; ferrotransferrin; insulin; a cytokine; gp120; β-actin; leukocyte function-associated antigen 1 (LFA-1; CD11a/CD18); Mac-1 (CD11b/CD18); glycophorin; laminin; collagen; fibronectin; vitronectin; an integrin, ankyrin; fibrinogen, Factor X; inter-cellular adhesion molecule 1 (ICAM-1); inter-cellular adhesion molecule 2 (ICAM-2); spectrin, fodrin; CD4; a cytokine receptor; an insulin receptor; a transferrin receptor; Fe+++; polymyxin B; endotoxin-neutralizing protein (ENP); an antibody-specific antigen; avidin; streptavidin; and biotin. Non-radioactive labeling methods, techniques, and reagents are reviewed in: Non-Radioactive Labeling, A Practical Introduction, Garman (1997) Academic Press, San Diego. In some embodiments, the terms "label" and "reporter" are used interchangeably.

Sequencing

Universal tags with a 5' universal tag comprising at least one non-natural nucleobase complementary to a corresponding non-natural nucleobase can also be used in sequencing processes. Sequencing processes determine the order of the nucleotide bases in a DNA or RNA sequence. For example, chain-termination processes start with a single-stranded DNA (or RNA) template, a sequencing primer, a polymerase, ddNTPs, and modified nucleotides that terminate elongation (for example ddNTPs). The modified nucleotides may be added at a lower concentration than the dNTPs to allow strand elongation, and the concentration of dNTPs and ddNTPs is determined based on their relative preference as a substrate for the polymerase enzyme.

After elongation, the newly synthesized fragments are heat denatured and separated by size. The separate fragments are then imaged for identification of the terminal nucleotide base that terminated elongation. In this manner, the specific nucleotide base is identified for an entire strand.

In on such technique, nucleic acid fragments can be tagged with radioactive elements for radiolabelling. In another technique, the sequencing primer may be labeled at the 5' end with a fluorescent dye for tagging (dye-primer sequencing). In yet another technique, the chain terminators can be labeled with a dye (dye-terminator sequencing). These and other sequencing processes can be adapted for use with the universal tags.

Articles of Manufacture

The present invention provides articles of manufacture (e.g., kits) comprising at least one universal tag. In certain embodiments, kits serve to facilitate the performance of a process, method, assay, analysis or manipulation of interest by assembling two or more components used to carry out the methods. Kits can contain any chemical reagent, enzyme, or equipment required for use of the method. In certain embodiments, kits contain components in pre-measured amounts to minimize the need for measurements by end-users. In certain embodiments, kits include instructions for performing one or more methods. In certain embodiments, the kit components are optimized to operate in conjunction with one another.

Other components of kits include an amplification primer with a sequencing tag, a corresponding sequencing primer, an amplification polymerase, sequencing polymerase, dNTP mix (for amplification), ddNTP/DNTP mix (for sequencing), and suitable buffers. In some embodiments, a second amplification primer and corresponding sequencing primer may also be present.

When used in kits, the amplification primer containing the universal tag can be made sequence-specific for a given target sequence. The sequencing primer can be labeled or unlabeled. If the sequencing primer is labeled, the label chosen will be suitable for use in the intended application. The primers can be packaged in suitable containers, such as tubes or ampules, and can be packaged in a dried (e.g., lyophilized) form, or in an aqueous form. If necessary, the articles of manufacture in the kits can be chilled or frozen during shipping and/or storage. Any article of manufacture comprising universal tag can further include a description of the product, specifications of the product, or instructions for use of the product.

In addition, kits can also include, for example but are not limited to, apparatus and reagents for sample collection and/or purification, apparatus and reagents for product collection and/or purification, sample tubes, holders, trays, racks, dishes, plates, instructions to the kit user, solutions, buffers or other chemical reagents, suitable samples to be used for standardization, normalization, and/or control samples. Kits can also be packaged for convenient storage and shipping, for example, in a box having a lid.

The sequencing primer provided in the kits may or may not be labeled. In other embodiments, the invention provides kits comprising sequencing primers as well as means for labeling the oligomers. In other embodiments, the invention provides kits comprising a labeled or unlabeled universal tag as well as some means (for example an apparatus or reagent) for the visualization or detection the tags.

The invention also provides kits to facilitate use of the universal tags in various methods, e.g., any method that involves sequence-specific hybridization. Materials and reagents to carry out these methods can be provided in kits to facilitate execution of the methods. A kit comprises at least one universal tagged primer and at least one sequencing primer, and optionally can additionally comprise a number of additional components, including but not limited to (i) one or more buffers; (ii) one or more nucleotide triphosphates; (iii) a nucleic acid amplification master mix; (iv) one or more polymerase enzymes, or (v) reagents or equipment suitable for the isolation/purification of a nucleic acid product. In one embodiment, the kit comprises at least two universal tagged primers suitable for use as primers in a PCR reaction.

In some embodiments, the present invention provides kits for conducting real-time PCR analysis. These kits can include, for example but are not limited to, reagents for the collection of a sample, a reverse transcriptase, primer suitable for reverse transcriptase initiation and first strand cDNA synthesis, at least one universal tagged primer, a DNA-dependent DNA polymerase, free deoxyribonucleotide triphosphates, and reagents suitable for the isolation/purification of the cDNA molecules produced by the reaction.

In one embodiment providing kits, a single universal tagged primer is provided that is specific for a single target sequence. In other embodiments, multiple universal tagged primers specific for a plurality of targets are provided in the kit. In some embodiments, kits are provided having the universal tagged primers affixed to a solid phase or surface. In certain embodiments, the kits may be used to sequence at least one target nucleic acid template.

In still other embodiments, there are kits for the analysis of gene expression using the universal sequencing primers. These kits can include multiple universal tagged primers affixed to a suitable array or chip configuration, as well as reagents required for the detection/visualization of hybridized complexes.

In still another aspect, there are kits comprising a universal tagged primer comprising a plurality of purine nucleotides, where at least one purine nucleotide comprises a non-natural nucleobase, coupled to a backbone consisting of ribose or deoxyribose, and phosphate, wherein the purine nucleotides of the universal tagged primer are complementary to a plurality of pyrimidine nucleotides of a polynucleotide template, where at least one pyrimidine nucleotide comprises a non-natural nucleobase complementary to the non-natural purine nucleobase. Kits comprising universal tagged primers may further include other reagents necessary for primer-initiated synthesis, including dNTPs and suitable buffer components.

In another aspect, there are kits comprising a universal tagged primer comprising one or more regions having a plurality of purine and/or pyrimidine nucleotides, where at least one purine and/or pyrimidine nucleotide is a non-natural nucleobase, coupled to a backbone of ribose or deoxyribose, and phosphate, wherein the purine nucleotides of the universal tagged primer are complementary to a polynucleotide template comprising one or more regions having a plurality of purine and/or pyrimidine nucleotides, where at least one purine and/or pyrimidine nucleotide is a non-natural pyrimidine nucleobase complementary to at least one other non-natural nucleobase present in the primer, coupled to a backbone of ribose or deoxyribose, and phosphate.

Such kits may be useful in diagnostic and research settings.

Applications and Methods of Use

The described compositions and methods find use in a variety of applications. It is not intended that the invention find use in only the few applications discussed herein, as one familiar with the art will immediately recognize a variety of uses for the universal tags with at least one non-natural nucleobase. The uses cited herein are intended to be exemplary and not limiting, and such examples are not exhaustive. It is understood that use is not limited to any particular application cited herein, as the invention finds use with any protocol that incorporates universal tags as probes or primers.

Use in Hybridization Reactions

The nucleobase oligomers find use in any method involving hybridization, i.e., the forming of a complex between two complementary nucleobase sequences. The complementarity need not be 100%, as effective hybridizations can occur when there is less than 100% complementarity.

The potential uses of the universal tags are not in any way limited. Thus, one familiar with the art recognizes that the specific conditions to be used in hybridization reactions as practiced using compositions are similarly unlimited, and are dependent on the particular application and the primary sequence of the universal tags used. A wide variety of sources are available that describe hybridization conditions for particular application; see, e.g., Ausubel et al. (eds.), Current Protocols in Molecular Biology, Chapter 22, "Nucleic Acid Arrays," John Wiley & Sons, Inc., New York [1994]; and M. Schena, (ed.), Microarray Biochip Technology, BioTechnique Books, Eaton Publishing, Natick, Mass. [2000].

Immobilization on a Solid Support (Arrays)

In one aspect, there are compositions and methods for making and using nucleobase oligomers with a universal tag that are affixed to a solid support. A wide variety of solid supports find use with the invention, and it is not intended that the invention be limited to the use of any particular type of solid support. Similarly, it is not intended that the manner in which the nucleobase oligomers are affixed to the solid support be limited in any way.

In one embodiment, the support-bound nucleobase oligomers with a universal tag form an array (e.g., a chip) of oligomers. Detailed methods for making and using arrays comprising polymeric nucleobase structures (e.g., nucleic acid, modified nucleic acids, nucleic acid analogs, or chimeric structures) are well-known in the art and are described in many sources. See, e.g., Ausubel et al. (eds.), Current Protocols in Molecular Biology, Chapter 22, "Nucleic Acid Arrays," John Wiley & Sons, Inc., New York [1994]; and M. Schena, (ed.), Microarray Biochip Technology, BioTechnique Books, Eaton Publishing, Natick, Mass. [2000]. Any methods for the synthesis and use of nucleic acids, modified nucleic acids and nucleic acid analogs with solid supports, and more specifically arrays, can be used.

Because the location and sequence of each support bound oligomer with a universal tag is known, arrays can be used to simultaneously detect, identify and/or quantitate the presence or amount of one or more target sequences in a sample. For example, a target sequence can be captured by the complementary nucleobase oligomer on the array surface and then the complex containing the target sequence can be detected. Since the sequence of the nucleobase oligomer is known at each location on the surface of the array, the sequence of target sequence(s) can be directly detected, identified and/or quantitated by determining the location of a detectable signal generated on the array. Thus, arrays are useful in diagnostic applications or in screening compounds, e.g., during development of therapeutic compounds.

In one embodiment, the oligomers with a universal tag can be synthesized on the surface in a manner suitable for deprotection but not cleavage from the synthesis support (see, e.g., Weiler et al., Hybridization based DNA screening on peptide nucleic acid (PNA) oligomer arrays," Nucl. Acids Res., 25(14):2792-2799 (1997)). In still another embodiment, one or more nucleobase oligomers with a universal tag can be covalently linked to a surface by the reaction of a suitable functional group on the oligomer or the universal tag with a functional group of the surface (see, e.g., Geiger et al., PNA Array technology in molecular diagnostics, Nucleosides & Nucleotides 17(9-11):1717-1724 (1998)). This method is advantageous since the oligomers immobilized on the surface can be highly purified and attached using a defined chemistry, thereby possibly minimizing or eliminating non-specific interactions.

Methods for the chemical attachment of nucleobase oligomers with universal tags to solid support surfaces can involve the reaction of a nucleophilic group, (e.g., an amine or thiol) of the oligomer or the universal tag to be immobilized, with an electrophilic group on the solid support surface. Alternatively, the nucleophile can be present on the support and the electrophile (e.g., activated carboxylic acid) can be present on the oligomer.

Conditions suitable for the immobilization of a nucleobase oligomer with a universal tag to a surface are widely known in the art. The immobilization reaction to a solid support is analogous to a labeling reaction, where the label is substituted with the surface to which the polymer is to be linked. It is not intended that the invention be limited to any particular immobilization chemistry or method.

Numerous types of solid supports derivatized with amino groups, carboxylic acid groups, isocyantes, isothiocyanates and malimide groups are commercially available. Non-limiting examples of suitable solid supports include chips of any type (e.g., arrays), membranes, glass, controlled pore glass, polystyrene particles (beads), silica and gold nanoparticles. All of the above recited methods of immobilization are not intended to be limiting in any way but are merely provided by way of illustration.

Detection/Identification of Biological Organisms

The nucleobase oligomers with universal tags find use in the detection, identification and/or enumeration of biological organisms, and especially, pathogens. Such organisms can include viruses, bacteria and eucarya in food, beverages, water, pharmaceutical products, personal care products, dairy products or in samples of plant, animal, human or environmental origin. The nucleobase oligomers with universal tags find use in the analysis of raw materials, equipment, products or processes used to manufacture or store food, beverages, water, pharmaceutical products, personal care products dairy products or environmental samples. Additionally, the nucleobase oligomers find use in the detection of pathogens (e.g., various bacteria, viruses and eucarya) in clinical specimens, equipment, fixtures or products used to treat humans or animals as well as in clinical samples and clinical environments. For example, the analysis for microorganisms of interest can be performed using FISH or multiplex FISH using probes generated by the invention described herein (See: BP U.S. application Ser. Nos. 09/335,629 and 09/368,089).

The compositions, methods, kits, libraries and arrays with a universal tag are particularly useful in areas such as expression analysis, single nucleotide polymorphism (SNP) analysis, genetic analysis of humans, animals, fungi, yeast, viruses, and plants (including genetically modified organisms), therapy monitoring, pharmacogenomics, pharmacogenetics, epigenomics, and high throughput screening operations.

EXAMPLES

Example 1

A universal sequencing protocol was tested by amplifying and sequencing the gene for the carboxyl terminus of Hsc70-interacting protein (CHIP). Two sets of amplification primers were examined. The length of the 5'-overhang (or tag) used to create a primer binding region for the sequencing reaction was changed between the two sets (Table 1). 2'-Deoxyisocytidine (F) and 2'-deoxyisoguanosine (J) were included in the tag sequences. The CHIP-specific portions of the amplification primers (underlined in Table 1) were identical in both sets.

TABLE 1

Amplification and Sequencing Primers

| Primer Name | Primer Type | Sequence | SEQ ID NO: |
|---|---|---|---|
| LF Amp | Forward Amplification | CGFTGACTFJJACAAGGAGCAGGGCAATCGTC | 1 |
| SF Amp | Forward Amplification | CFGFCTFJJACAAGGAGCAGGGCAATCGTC | 2 |
| LF Seq | Sequencing | CGFTGACTFJJAC | 3 |
| SF Seq | Sequencing | CFGFCTFJJAC | 4 |
| LR Amp | Reverse Amplification | AGJTGAGFGCFFJAGCAGGTAGTCGGGGATGTCTC | 5 |
| SR Amp | Reverse Amplification | GFGFGCFFJAGCAGGTAGTCGGGGATGTCTC | 6 |
| LR Seq | Sequencing | AGJTGAGFGCFFJAG | 7 |
| SR Seq | Sequencing | GFGFGCFFJAG | 8 |

Amplification

A 606 nucleotide fragment of CHIP in the green fluorescent protein fusion vector pEGFP-C3 (Ballinger, 1999) was amplified with either the LF/LR amplification primer pair or the SF/SR amplification primer pair and TITANIUM® Taq polymerase (BD Biosciences), using a Mastercycler ep gradient S thermal cycler (Eppendorf). Thermal cycling conditions were 95° C. (60 s) followed by 40 cycles of 95° C. (30 s), 60° C. (60 s). Reaction solutions contained 10 pM each amplification primer (LF/LR or SF/SR), 50 ng plasmid, 2.5 mM each dNTP (including dFTP and dJTP), 0.4 uL of TITANIUM® Taq in TITANIUM® Taq buffer (20 uL total volume). Reactions were purified with MinElute PCR Purification spin columns.

Sequencing

Cycle sequencing was performed with the DYEnamic™ ET Dye Terminator Kit on a MegaBACE® 1000 Sequencer (GE Healthcare). Bidirectional sequencing was performed in two reactions with DYEnamic™ ET reagent premix (8 uL), 5 uM individual sequencing primer (1 uL), and purified amplicon (1 uL of 1 to 40 dilution with water) in a total volume of 20 uL. The cycling conditions were 95° C. (20 s), 50° C. (15 s), 60° C. (60 s), repeated 20-30 times. The extension step worked with a 50° C. step replacing the 60° C. step, as well. Either the LF/LR or the SF/SR sequencing primers were used. Sequencing reactions were purified with Illustra autoseq G50 spin columns and analyzed as recommended on the MegaBACE® 1000.

Results

Amplification product lengths were verified with a 2100 Bioanalyzer (Agilent) or a TRUGENE® System (Siemens) using fragment length analysis software for reactions using either the LF/LR or the SF/SR amplification primer sets. Sequencing analysis gave the expected CHIP sequence with either LF/LR sequencing primers or the SF/SR sequencing primers. The sequencing reaction always aborted when encountering F or J positions introduced to the amplicon by the sequencing primers.

It is to be understood that the foregoing descriptions of embodiments of the present invention are exemplary and explanatory only, are not restrictive of the invention, as claimed, and merely illustrate various embodiments of the invention. It will be appreciated that other particular embodiments consistent with the principles described in the specification but not expressly disclosed may fall within the scope of the claims.

What is claimed is:

1. A kit for sequencing a polynucleotide target, comprising:
   (a) an amplification primer comprising:
      (i) a 3' target-specific nucleotide sequence; and
      (ii) a 5' non-target-specific universal sequencing tag comprising at least one natural nucleobase that is not target specific and at least three contiguous non-natural nucleobases, each capable of complementary binding to a corresponding non-natural nucleobase, wherein the at least three contiguous non-natural nucleobases are capable of being replicated during amplification by an amplification polymerase but are not capable of being sequenced by a sequencing polymerase, whereby the portion of (ii) that is 5' to the at least three contiguous non-natural nucleobases cannot be sequenced; and
   (b) a universal sequencing primer comprising an oligonucleotide of the sequence comprising the 5' non-target-specific universal sequencing tag.

2. The kit of claim 1, further comprising an amplification polymerase.

3. The kit of claim 1, further comprising a sequencing polymerase.

4. The kit of claim 1, wherein each of the at least three contiguous non-natural nucleobases is independently selected from the group consisting of non-Watson-Crick complementary nucleobase analogs.

5. The kit of claim 1, wherein each of the at least three contiguous non-natural nucleobases is independently selected from the group consisting of Watson-Crick complementary nucleobase analogs having hydrogen bonding interactions that can be discriminated from natural nucleobase pairs.

6. The kit of claim 1, wherein each of the three contiguous non-natural nucleobases is independently selected from the group consisting of isocytosine, isoguanine, and 5-methylisocytosine.

7. The kit of claim 1, wherein at least one of the at least three contiguous non-natural nucleobases is isocytosine.

8. The kit of claim 1, wherein at least one of the at least three contiguous non-natural nucleobases is isoguanine.

9. The kit of claim 1, wherein at least one of the at least three contiguous non-natural nucleobases is 5-methylisocytosine.

10. The kit of claim 1, wherein the 5' non-target-specific universal sequencing tag is further defined as comprising at least one natural nucleobase that is not target specific and at least four non-natural nucleobases, wherein at least three of the four non-natural nucleobases are contiguous, wherein each of the at least four non-natural nucleobases is capable of complementary binding to a corresponding non-natural nucleobase, and wherein the at least four non-natural nucleobases are capable of being replicated during amplification by an amplification polymerase but are not capable of being sequenced by a sequencing polymerase, whereby the portion of (ii) that is 5' to the at least four non-natural nucleobases cannot be sequenced.

11. The kit of claim 1, wherein the 5' non-target-specific universal sequencing tag comprises at least one natural nucleobase that is not target specific at the 3' end thereof, whereby the at least one non-target-specific natural nucleobase is contiguous to the target-specific nucleotide sequence.

12. The kit of claim 1, wherein the 5' non-target-specific universal sequencing tag is further defined as comprising at least three natural nucleobases that are not target specific, wherein the at least three non-target-specific natural nucleobases are disposed at the 3' end of the 5' non-target-specific universal sequencing tag and are contiguous to the target-specific nucleotide sequence.

13. A kit for sequencing a polynucleotide target, comprising:
(a) an amplification primer comprising:
   (i) a 3' target-specific nucleotide sequence; and
   (ii) a 5' non-target-specific universal sequencing tag comprising at least one natural nucleobase that is not target specific and at least three contiguous non-natural nucleobases, each capable of complementary binding to a corresponding non-natural nucleobase;
(b) a universal sequencing primer comprising an oligonucleotide of the sequence comprising the 5' non-target-specific universal sequencing tag;
(c) an amplification polymerase; and
(d) a sequencing polymerase; and
wherein the at least three contiguous non-natural nucleobases of (a)(ii) are capable of being replicated during amplification by the amplification polymerase but are not capable of being sequenced by the sequencing polymerase, whereby the portion of (a)(ii) that is 5' to the at least three contiguous non-natural nucleobases cannot be sequenced.

14. The kit of claim 13, wherein each of the at least three contiguous non-natural nucleobases is independently selected from the group consisting of non-Watson-Crick complementary nucleobase analogs having hydrogen bonding interactions that can be discriminated from natural nucleobase pairs.

15. The kit of claim 13, wherein each of the three contiguous non-natural nucleobases is independently selected from the group consisting of isocytosine, isoguanine, and 5-methylisocytosine.

16. The kit of claim 13, wherein the 5' non-target-specific universal sequencing tag is further defined as comprising at least one natural nucleobase that is not target specific and at least four non-natural nucleobases, wherein at least three of the four non-natural nucleobases are contiguous, wherein each of the at least four non-natural nucleobases is capable of complementary binding to a corresponding non-natural nucleobase.

17. The kit of claim 13, wherein the at least one natural nucleobase that is not target specific of the 5' non-target-specific universal sequencing tag is at the 3' end thereof, whereby the at least one non-target-specific natural nucleobase is contiguous to (i).

18. A kit for sequencing a polynucleotide target, comprising:
(a) an amplification primer comprising:
   (i) a 3' target-specific nucleotide sequence; and
   (ii) a 5' non-target-specific universal sequencing tag comprising: at least three contiguous non-natural nucleobases, wherein each of the at least three contiguous non-natural nucleobases is capable of complementary binding to a corresponding non-natural nucleobase, and wherein each of the three contiguous non-natural nucleobases is independently selected from the group consisting of isocytosine, isoguanine, and 5-methylisocytosine; and
   at least one natural nucleobase that is not target specific, whereby the at least one non-target-specific natural nucleobase is at the 3' end of the universal sequencing tag and is contiguous to (i);
(b) a universal sequencing primer comprising an oligonucleotide of the sequence comprising the 5' non-target-specific universal sequencing tag;
(c) an amplification polymerase; and
(d) a sequencing polymerase; and
wherein the at least three contiguous non-natural nucleobases of (a)(ii) are capable of being replicated during amplification by the amplification polymerase but are not capable of being sequenced by the sequencing polymerase, whereby the portion of (a)(ii) that is 5' to the at least three contiguous non-natural nucleobases cannot be sequenced.

\* \* \* \* \*

SEQUENCE LISTING

<160> NUMBER OF SEQ ID NOS: 8

<210> SEQ ID NO 1
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is isocytosine or isoguanine
<220> FEATURE:
<221> NAME/KEY: misc_feature
<222> LOCATION: (9)..(11)
<223> OTHER INFORMATION: n is isocytosine or isoguanine

<400> SEQUENCE: 1
cgntgactnn nacaaggagc agggcaatcg tc        32

<210> SEQ ID NO 2
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(2)
<223> OTHER INFORMATION: n is isocytosine or isoguanine
<220> FEATURE:
<221> NAME/KEY: misc_feature
<222> LOCATION: (4)..(4)
<223> OTHER INFORMATION: n is isocytosine or isoguanine
<220> FEATURE:
<221> NAME/KEY: misc_feature
<222> LOCATION: (7)..(9)
<223> OTHER INFORMATION: n is isocytosine or isoguanine

<400> SEQUENCE: 2
cngnctnnna caaggagcag ggcaatcgtc        30

<210> SEQ ID NO 3
<211> LENGTH: 13

-continued

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is isocytosine or isoguanine
<220> FEATURE:
<221> NAME/KEY: misc_feature
<222> LOCATION: (9)..(11)
<223> OTHER INFORMATION: n is isocytosine or isoguanine

<400> SEQUENCE: 3
cgntgactnn nac                                                     13

<210> SEQ ID NO 4
<211> LENGTH: 11
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(2)
<223> OTHER INFORMATION: n is isocytosine or isoguanine
<220> FEATURE:
<221> NAME/KEY: misc_feature
<222> LOCATION: (4)..(4)
<223> OTHER INFORMATION: n is isocytosine or isoguanine
<220> FEATURE:
<221> NAME/KEY: misc_feature
<222> LOCATION: (7)..(9)
<223> OTHER INFORMATION: n is isocytosine or isoguanine

<400> SEQUENCE: 4
cngnctnnna c                                                       11

<210> SEQ ID NO 5
<211> LENGTH: 35
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is isocytosine or isoguanine
<220> FEATURE:
<221> NAME/KEY: misc_feature
<222> LOCATION: (8)..(8)
<223> OTHER INFORMATION: n is isocytosine or isoguanine
<220> FEATURE:
<221> NAME/KEY: misc_feature
<222> LOCATION: (11)..(13)
<223> OTHER INFORMATION: n is isocytosine or isoguanine

<400> SEQUENCE: 5
agntgagngc nnnagcaggt agtcggggat gtctc                             35

<210> SEQ ID NO 6
<211> LENGTH: 31
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(2)
<223> OTHER INFORMATION: n is isocytosine or isoguanine
<220> FEATURE:
<221> NAME/KEY: misc_feature
<222> LOCATION: (4)..(4)
```

```
<223> OTHER INFORMATION: n is isocytosine or isoguanine
<220> FEATURE:
<221> NAME/KEY: misc_feature
<222> LOCATION: (7)..(9)
<223> OTHER INFORMATION: n is isocytosine or isoguanine

<400> SEQUENCE: 6
gngngcnnna gcaggtagtc ggggatgtct c                                      31

<210> SEQ ID NO 7
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is isocytosine or isoguanine
<220> FEATURE:
<221> NAME/KEY: misc_feature
<222> LOCATION: (8)..(8)
<223> OTHER INFORMATION: n is isocytosine or isoguanine
<220> FEATURE:
<221> NAME/KEY: misc_feature
<222> LOCATION: (11)..(13)
<223> OTHER INFORMATION: n is isocytosine or isoguanine

<400> SEQUENCE: 7
agntgagngc nnnag                                                        15

<210> SEQ ID NO 8
<211> LENGTH: 11
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(2)
<223> OTHER INFORMATION: n is isocytosine or isoguanine
<220> FEATURE:
<221> NAME/KEY: misc_feature
<222> LOCATION: (4)..(4)
<223> OTHER INFORMATION: n is isocytosine or isoguanine
<220> FEATURE:
<221> NAME/KEY: misc_feature
<222> LOCATION: (7)..(9)
<223> OTHER INFORMATION: n is isocytosine or isoguanine

<400> SEQUENCE: 8
gngngcnnna g                                                            11
```